US009527883B2

(12) United States Patent
Savage et al.

(10) Patent No.: US 9,527,883 B2
(45) Date of Patent: Dec. 27, 2016

(54) METHODS FOR THE SYNTHESIS OF CERAGENINS

(71) Applicants: Paul B. Savage, Mapleton, UT (US); Jared Lynn Randall, Plymouth, NY (US)

(72) Inventors: Paul B. Savage, Mapleton, UT (US); Jared Lynn Randall, Plymouth, NY (US)

(73) Assignee: BRIGHAM YOUNG UNIVERSITY, Provo, UT (US)

( * ) Notice: Subject to any disclaimer, the term of this patent is extended or adjusted under 35 U.S.C. 154(b) by 0 days.

(21) Appl. No.: 15/135,900

(22) Filed: Apr. 22, 2016

(65) Prior Publication Data

US 2016/0311852 A1   Oct. 27, 2016

Related U.S. Application Data

(60) Provisional application No. 62/151,026, filed on Apr. 22, 2015.

(51) Int. Cl.
C07J 41/00 (2006.01)
C07J 75/00 (2006.01)

(52) U.S. Cl.
CPC ............. C07J 75/00 (2013.01); C07J 41/0066 (2013.01); C07J 41/0088 (2013.01)

(58) Field of Classification Search
CPC .................................. C07J 9/005; C07J 41/00
See application file for complete search history.

(56) References Cited

U.S. PATENT DOCUMENTS

| | | | |
|---|---|---|---|
| 4,661,341 A | 4/1987 | Benedict et al. |
| 4,842,593 A | 6/1989 | Jordan et al. |
| 4,865,855 A | 9/1989 | Hansen et al. |
| 4,972,848 A | 11/1990 | Di Domenico |
| 5,025,754 A | 6/1991 | Plyler |
| 5,286,479 A | 2/1994 | Garlich et al. |
| 5,310,545 A | 5/1994 | Eisen |
| 5,356,630 A | 10/1994 | Laurencin et al. |
| 5,364,650 A | 11/1994 | Guthery |
| 5,380,839 A | 1/1995 | McCall et al. |
| 5,552,057 A | 9/1996 | Hughes et al. |
| 5,721,359 A | 2/1998 | Dunn et al. |
| 6,117,332 A | 9/2000 | Hatch et al. |
| 6,228,393 B1 | 5/2001 | DiCosmo et al. |
| 6,350,738 B1 | 2/2002 | Savage et al. |
| 6,486,148 B2 | 11/2002 | Savage et al. |
| 6,562,318 B1 | 5/2003 | Filler |
| 6,673,771 B1 | 1/2004 | Greene et al. |
| 6,767,904 B2 | 7/2004 | Savage et al. |
| 6,803,066 B2 | 10/2004 | Traeder |
| 6,872,303 B2 | 3/2005 | Knapp et al. |
| 6,939,376 B2 | 9/2005 | Shulze et al. |
| 7,282,214 B2 | 10/2007 | Willcox et al. |
| 7,381,439 B2 | 6/2008 | Hilgren et al. |
| 7,598,234 B2 | 10/2009 | Savage et al. |
| 7,659,061 B2 | 2/2010 | Hendl et al. |
| 7,754,705 B2 | 7/2010 | Savage et al. |
| 7,854,941 B2 | 12/2010 | Urban et al. |
| 7,993,903 B2 | 8/2011 | Hayakawa et al. |
| 8,211,879 B2 | 7/2012 | Savage et al. |
| 8,529,681 B1 | 9/2013 | Hibbs et al. |
| 8,623,416 B2 | 1/2014 | Zasloff et al. |
| 8,691,252 B2 | 4/2014 | Savage |
| 8,784,857 B2 | 7/2014 | Savage |
| 8,932,614 B2 | 1/2015 | Savage et al. |
| 8,945,217 B2 | 2/2015 | Savage et al. |
| 8,975,310 B2 | 3/2015 | Savage |
| 9,155,746 B2 | 10/2015 | Genberg et al. |
| 9,161,942 B2 | 10/2015 | Genberg et al. |
| 9,314,472 B2 | 4/2016 | Beus et al. |
| 9,345,655 B2 | 5/2016 | Vazquez et al. |
| 9,387,215 B2 | 7/2016 | Beus et al. |

(Continued)

FOREIGN PATENT DOCUMENTS

| | | |
|---|---|---|
| CN | 101378761 | 3/2009 |
| CN | 102172356 | 9/2011 |
| EP | 0341951 | 11/1989 |
| EP | 1208844 | 5/2002 |
| JP | 02014741 | 1/1990 |
| JP | 06153779 | 6/1994 |
| JP | 07501826 | 2/1995 |
| JP | 09248454 | 9/1997 |
| JP | 2002505292 | 2/2002 |
| JP | 2002255771 | 9/2002 |

(Continued)

OTHER PUBLICATIONS

Zaragoza Dorwald, Side Reactions in Organic Synthesis, 2005, WILEY-VCH Verlag GmbH & Co. KGaA, Weinheim, Preface. p. IX.*
Li et al, Journal of the American Chemical Society, Incremental Conversion of Outer-Membrane Permeabilizers into Potent Antibiotics for Gram-Negative Bacteria, 1999, 121, pp. 931-940.*
U.S. Appl. No. 13/783,007, filed Mar. 1, 2013, Savage.
U.S. Appl. No. 14/866,213, filed Sep. 25, 2015, Savage.
U.S. Appl. No. 15/076,313, filed Mar. 21, 2016, Beus et al.
U.S. Appl. No. 15/135,928, filed Apr. 22, 2016, Savage et al.

(Continued)

*Primary Examiner* — Paul A Zucker
(74) *Attorney, Agent, or Firm* — Workman Nydegger

(57) ABSTRACT

Disclosed herein are methods of making ceragenin compounds for treating, preventing, or diagnosing diseases, disorders, or conditions associated with bacterial or viral infections, cancer, inflammation, and osteogenesis. Ceragenin compounds display broad spectrum antibacterial activity utilizing a mode of action similar to antimicrobial peptides, but without the high synthesis costs and susceptibility to proteolytic degradation. Ceragenin compounds reproduce the amphiphilic morphology found in many antimicrobial peptides and display potent and diverse biological activities, including anti-bacterial, anti-cancer, anti-inflammatory, bone growth promotion, and wound healing promotion.

17 Claims, 2 Drawing Sheets

(56) References Cited

U.S. PATENT DOCUMENTS

| | | |
|---|---|---|
| 2002/0091278 A1 | 7/2002 | Savage et al. |
| 2003/0099717 A1 | 5/2003 | Cabrera |
| 2004/0009227 A1 | 1/2004 | Yao |
| 2004/0058974 A1 | 3/2004 | Courtney et al. |
| 2004/0259445 A1 | 12/2004 | Hilfenhaus et al. |
| 2005/0032765 A1 | 2/2005 | Savage et al. |
| 2005/0075321 A1 | 4/2005 | Ahlem et al. |
| 2005/0244468 A1 | 11/2005 | Huang et al. |
| 2005/0267051 A1 | 12/2005 | Lee et al. |
| 2006/0062742 A1 | 3/2006 | Davis et al. |
| 2006/0269485 A1 | 11/2006 | Friedman et al. |
| 2007/0106393 A1 | 5/2007 | Miles et al. |
| 2007/0190066 A1 | 8/2007 | Savage et al. |
| 2007/0190067 A1 | 8/2007 | Savage et al. |
| 2007/0190558 A1 | 8/2007 | Savage et al. |
| 2008/0174035 A1 | 7/2008 | Winterton |
| 2008/0188819 A1 | 8/2008 | Kloke et al. |
| 2008/0279944 A1 | 11/2008 | Sawhney |
| 2009/0016973 A1 | 1/2009 | Ratcliff et al. |
| 2009/0054295 A1 | 2/2009 | Vicari et al. |
| 2009/0068122 A1 | 3/2009 | Pilch et al. |
| 2009/0252781 A1 | 10/2009 | Sawhney et al. |
| 2009/0324517 A1 | 12/2009 | Kline |
| 2010/0092398 A1 | 4/2010 | Reynolds |
| 2010/0226884 A1 | 9/2010 | Chang et al. |
| 2010/0330086 A1 | 12/2010 | Savage et al. |
| 2011/0091376 A1 | 4/2011 | Savage et al. |
| 2011/0123624 A1 | 5/2011 | Zasloff |
| 2012/0088733 A1 | 4/2012 | Kim et al. |
| 2012/0107382 A1 | 5/2012 | Savage et al. |
| 2013/0022651 A1 | 1/2013 | Savage |
| 2013/0236619 A1 | 9/2013 | Savage |
| 2013/0280312 A1 | 10/2013 | De Szalay |
| 2013/0280391 A1 | 10/2013 | Savage |
| 2014/0194401 A1 | 7/2014 | Genberg et al. |
| 2014/0219914 A1 | 8/2014 | Govindan et al. |
| 2014/0271761 A1 | 9/2014 | Savage et al. |
| 2014/0274913 A1 | 9/2014 | Savage et al. |
| 2014/0336131 A1 | 11/2014 | Savage et al. |
| 2014/0363780 A1 | 12/2014 | Vazquez et al. |
| 2015/0093423 A1 | 4/2015 | Savage et al. |
| 2015/0110767 A1 | 4/2015 | Savage et al. |
| 2015/0140063 A1 | 5/2015 | Savage |
| 2015/0203527 A1 | 7/2015 | Savage |
| 2015/0239928 A1 | 8/2015 | Savage |
| 2015/0258121 A1 | 9/2015 | Darien et al. |
| 2015/0258122 A1 | 9/2015 | Beus et al. |
| 2015/0258123 A1 | 9/2015 | Savage et al. |
| 2015/0314342 A1 | 11/2015 | Beus et al. |
| 2015/0366880 A1 | 12/2015 | Genberg et al. |
| 2015/0374719 A1 | 12/2015 | Genberg et al. |
| 2015/0374720 A1 | 12/2015 | Genberg et al. |
| 2016/0022702 A1 | 1/2016 | Savage et al. |
| 2016/0045421 A1 | 2/2016 | Vazquez et al. |
| 2016/0052959 A1 | 2/2016 | Savage |
| 2016/0096864 A1 | 4/2016 | Savage |
| 2016/0193232 A1 | 7/2016 | Beus et al. |

FOREIGN PATENT DOCUMENTS

| | | |
|---|---|---|
| JP | 2002534532 | 10/2002 |
| JP | 2002538093 | 11/2002 |
| JP | 2004506645 | 3/2004 |
| JP | 2010533051 | 10/2010 |
| JP | 2010538074 | 12/2010 |
| JP | 2011527702 | 11/2011 |
| JP | 2014500741 | 1/2014 |
| WO | WO 9524415 | 9/1995 |
| WO | WO 9944616 | 9/1999 |
| WO | WO 0042058 | 7/2000 |
| WO | WO 0214342 | 2/2002 |
| WO | WO02/067979 | 9/2002 |
| WO | WO03015757 | 2/2003 |
| WO | WO03090799 | 11/2003 |
| WO | WO2004082588 | 9/2004 |
| WO | WO 2004112852 | 12/2004 |
| WO | WO 2007089903 | 8/2007 |
| WO | WO 2007089906 | 8/2007 |
| WO | WO 2007089907 | 8/2007 |
| WO | WO 2007134176 | 11/2007 |
| WO | WO 2008038965 | 4/2009 |
| WO | WO 2009079066 | 6/2009 |
| WO | WO2010006192 | 1/2010 |
| WO | WO2010036427 | 4/2010 |
| WO | WO2010062562 | 6/2011 |
| WO | WO2011066260 | 6/2011 |
| WO | WO2011109704 | 9/2011 |
| WO | WO2012061651 | 5/2012 |
| WO | WO2013029055 | 2/2013 |
| WO | WO2013029059 | 2/2013 |
| WO | WO2013040269 | 3/2013 |
| WO | WO 2013109236 | 7/2013 |

OTHER PUBLICATIONS

U.S. Appl. No. 15/135,969, filed Apr. 22, 2016, Savage et al.

Alafort et al., "Lys and Arg in UBI: A specific site for a stable Tc-99m complex?", Nuclear Medicine and Biology 30 (2003) 605-615.

Alhanout K et al: "Squalamine as an example of a new potent antimicrobial agents class: a critical review.", Current Medicinal Chemistry 2010, vol. 17, No. 32, 2010, pp. 3909-3917.

Atiq-Ur-Rehman Li C et al: "Preparation of Amino Acid-Appended Cholic Acid Derivatives as Sensitizers of Gram-Negative Bacteria", Tetrahedron Letters, Elsevier, Amsterdam, NL, vol. 40, No. 10, Mar. 5, 1999 (Mar. 5, 1999), pp. 1865-1868, XP004155984, ISSN: 0040-4039, DOI: 10.1016/S0040-4039(99)00075-1.

Bellini et al., "Cholic and deoxycholic acids derivatives (Part I). Antimicrobial activity of cholane compounds", European J. of Medicinal Chem., 18(2), pp. 185-190, 1983.

Bellini et al., "Cholic and deoxycholic acids derivatives (Part II). Antimicrobial activity of cholane compounds", European J. of Medicinal Chem., 18(2), pp. 191-195, 1983.

Berge et al., "Pharmaceutical Salts", Journal of Pharmaceutical Sciences, Jan. 1977, vol. 66, No. 1, pp. 1-19.

Bridot et al., "Hybrid Gadolinium Oxide Nanoparticles: Multimodal Contrast Agents for in Vivo Imaging", Journal of American Chemical Society, vol. 129, No. 16, pp. 5076-5084, Mar. 31, 2007.

Britton et al, "Imaging bacterial infection with 99mTc-ciprofloxacin (Infection)", Journal of Clinical Pathology, vol. 55, pp. 817-823, Apr. 6, 2015.

Brown, "Bioisosteres in Medicinal Chemistry, First Edition", edited by Nathan Brown, 2012, Ch. 2 Classical Bioisosteres, pp. 1-52.

Bucki et al., "Resistance of the antibacterial agent ceragenin CSA-13 to inactivation by DNA or F-actin and its activity in cystic fibrosis sputum", Journal of Antimicrobial Chemotherapy (2007) 60: 535-545, 11 pages.

Bucki et al., "Salivary mucins inhibit antibacterial activity of the cathelicidin-derived LL-37 peptide but not the cationic steroid CSA-13", Journal of Antimicrobial Chemotherapy (2008) 62: 329-335, 7 pages.

Chin et al, "Antimicrobial Activities of Ceragenins against Clinical Isolates of Resistant *Staphylococcus aureas*", Antimicrobial Agents and Chemotherapy, vol. 51, No. 4, Apr. 2007, p. 1268-1273.

Clara et al., "Preclinical evaluation of magainin-A as a contraceptive antimicrobial agent", Fertility and Sterility 81 (5), pp. 1357-1365, 2004.

Ding, et al., "Origins of cell selectivity of cationic steroid antibiotics", Journal of American Chemical Society, Oct. 2004, pp. 13642-13648.

Dörwald, "Side reactions in organic synthesis", 2005, Wiley-VCH Verlag GmbH & co., KGAA Weinhelm, Preface. p. IX.

Epand et al., "Bacterial lipid composition and the antimicrobial efficacy of cationic steroid compounds (Ceragenins)", BBA, 2007, pp. 65-78.

Fichna et al., "Synthesis of Target-Specific Radiolabeled Peptides for Diagnostic Imaging", Bioconjugate Chem., 2003, 14, 3-17, American Chemical Society.

(56) References Cited

OTHER PUBLICATIONS

Fritsch et al, "In Vitro Activity of Nine Developmental Cationic Steroid Compounds (Ceragenins) against Clinical Isolates of Clostridium difficile", The 46th Interscience Conference on Antimicrobial Agents and Chemotherapy, Sep. 27, 2006, pp. 1-1.
Guan et al: "Preparation and Characterization of Cholic Acid-Derived Antimicrobial Agents with Controlled Stabilities", Organic Letters, American Chemical Society, US, vol. 2, No. 18, Sep. 7, 2000 (Sep. 7, 2000), pp. 2837-2840.
Guan et al: "Supporting Information: Preparation and Characterization of Cholic Acid-Derived Antimicrobial Agents with Controlled Stabilities", Organic Letters, Aug. 17, 2000 (Aug. 17, 2000), pp. 1-7, XP55017313, Retrieved from the Internet: URL:http://pubs.acs.org/doi/supp1/10.1021/o10062704/suppl file/o10062704sl.pdf.
Howell et al., "Ceragenins: A 1-18, class of Antiviral Compounds to Treat Orthopox Infections", Journal of Investigative Dermatology, vol. 129, No. 11, Jun. 11, 2009, pp. 2688-2675.
Isogai E et al: "Ceragenin CSA-13 exhibits antimicrobial activity against cariogenic and periodontopathic bacteria", Oral Microbiology and Immunology, vol. 24, No. 2, Apr. 2009 (Apr. 2009), pp. 170-172.
International Search Report for PCT Application No. PCT/US2009/047485 dated Feb. 17, 2010.
International Search Report for PCT Application No. PCT/US2011/059225 dated Jan. 31, 2012.
International Search Report for PCT Application No. PCT/US2012/047750, dated Oct. 5, 2012.
International Search Report for PCT Application No. PCT/US2012/055244 dated Dec. 5, 2012.
International Search Report for PCT Application No. PCT/US2012/055248 dated Feb. 14, 2013.
International Search Report for PCT Application No. PCT/US2013/038090, Mailed Date: Jul. 24, 2013.
International Search Report for PCT Application No. PCT/US2014/034986 dated Aug. 28, 2014.
International Search Report for PCT Application No. PCT/US2013/065510 dated Apr. 30, 2015.
International Search Report for PCT Application No. PCT/US2015/020166 dated Sep. 2, 2015.
International Search Report for PCT Application No. PCT/US2015/038029 dated Sep. 29, 2015.
International Search Report for PCT Application No. PCT/US2015/046412 dated Dec. 1, 2015.
International Search Report for PCT Application No. PCT/US2015/054434 dated Dec. 23, 2015.
Iuliano, "Synthesis of four cholic acid-based CSPs containing 2-naphthyl carbamate and 3,5-dinitrophenylcarbamate moieties and their evaluation in the HPLC resolution of racemic compounds", Tetrahedron: Asymmetry 13 (2002) 1265-1275.
Lai, et al., "Controlled Released of a Bactericidal Ceragenin-Polymer Conjugate", Sep. 27, 2006, p. 1, 46th Annual Interscience Conference on Antimicrobial Agents and Chemotherapy.
Lankinen et al., "Ga-Dota-Peptide Targeting VAP-1 for In Vivo Evaluation of Inflammatory and Infectious Bone Conditions", 52nd Annual Meeting of the Orthopaedic Research Society.
Leszczynska et al., "Potential of ceragenin CSA-13 and its mixture with pluronic F-127 as treatment of topical bacterial infections", Journal of Applied Microbiology, vol. 110, No. 1, Oct. 21, 2010, pp. 229-238.
Li, et al., "Antimicrobial Activities of Amine- and Guanidine-functionalized Cholic Acid Derivatives", Antimicrobial Agents and Chemotherapy, American Society for Microbiology, Washington DC, US, vol. 43, No. 6, Jun. 1999, pp. 1347-1349.
Li et al., "Incremental conversion of Outer-Membrane Permeabilizers into Potent Antibiotics for Gram-Negative Bacteria", J. Am. Chem. Soc. 1999, 121, 931-940.
Lowe et al., "Effect of Hydrophobicity of a Drug on its Release from Hydrogels with Different Topological Structures" Journal of Polymer Science (1999) 73: 1031-1039 (9 pages).

Massoud et al., "Molecular imaging in living subjects: seeing fundamental biological processes in a new light", Genes & Development 17: 545-580 2003, Cold Spring Harbor Laboratory Press.
Muñoz-Juárez et al., "Wide-Lumen Stapled Anastomosis vs. Conventional End-to-End Anastomosis in the Treatment of Crohn's Disease", Dis Colon Rectum 2001 ; 44: No. 1, 20-26).
Perry et al., "Assessing peri-implant tissue infection prevention in a percutaneous model", Journal of Biomedical Materials Research Part B: Applied Biomaterials, vol. 02B, Nov. 19, 2009, pp. 397-408.
Pitten F-A, et al., "Efficacy of Cetylpyridinium Chloride Used as Oropharyngeal Antiseptic" Arzenimittel Forschung. Drug Research, ECV Editio Cantor Verlag, Aulendorf, DE, vol. 51, No. 7, Jan. 1, 2001, pp. 588-595.
Roohi et al., Prepration, quality control and biological evaluation of 99m-Tc-labelled cationic steroid antibiotic (CSA-13), Radiochim. Acta 197, 57-62 (2009).
Savage, et al., "Antibacterial Activities of Thin Films Containing Ceragenins", Microbial Surfaces: Structure, Interactions and Reactivity, ACS, May 30, 2008, pp. 65-78.
Paul B. Savage, et al: "Antibacterial Properties of cationic steroid antibiotics", FEMS Microbiology Letters, vol. 217, Nov. 2002, pp. 1-7.
Savage et al, "Thin Films Containing Ceragenins Prevent Biofilm Formation on Endotracheal Tubes", $9^{th}$ International Federation of Infection Control Congress, Oct. 14, 2008, pp. 1-1.
P. B. Savage, et al., "Use of a Ceragenin-Based Coating to Prevent Bacterial Colonization of Urinary Catheters", 48th Annual Interscience Conference on Anti-Microbial Agents & Chemotherapy, Oct. 26, 2008, pp. 1-1.
Schmidmaier et al., "Local Application of Growth Factors (Insulin-Like Growth Factor-1 and Transforming Growth Factor-β1) From a Biodegradable Poly(D, L-lactide) Coating of Osteosynthetic Implants Accelerates Fracture Healing in Rats", Bone vol. 28 No. 4, Apr. 2001.
Shi et al., "Multi-center randomized double-blind clinical trial on efficacy of a mouthwash containing 0.1% cetylpiridinium chloride on gingivitis and plaque and its safety", Chinese Journal of Evidence-Based Medicine (Sep. 2003, vol. 3, No. 3, pp. 171-177).
Sinclair et al., "Development of a broad spectrum polymer-released antimicrobial coating for the prevention of resistant strain bacterial infections", Journal of Biomedical Materials Research Part A, vol. 100A, No. 10, May 24, 2012, pp. 2732-2738.
Steeneveld et al., "Cow-specific treatment of clinical mastitis: an economic approach", Journal of Dairy Science vol. 94, Jan. 2011, pp. 174-188.
Suzuki et al., "Molecular Genetics of Plant Sterol Backbone Synthesis", 2007; Lipids; 42: 47-54.
Van Bambeke et al: "The bacterial envelope as a target for novel anti-MRSA antibiotics", Trends in Pharmacological Sciences, Elsevier, Haywarth, GB, vol. 29, No. 3, Feb. 11, 2008 (Feb. 11, 2008), pp. 124-134.
Van Den Bogaard et al., "Antibiotic Usage in Animals: Impact on Bacterial Resistance and Public Health"; 1999; Drugs; 58 (4): 589-607.
Welling et al., "Radiochemical and biological characteristics of 99m-Tc-UBI 29-41 for imaging of bacterial infections", Nuclear Medicine and Biology 29 (2002) 413-422.
Williams et al., "In vivo efficacy of a silicone-cationic steroid antimicrobial coating to prevent implant-related infection", Biomaterials, Nov. 2012: 33(33): 8641-8656 (Department of Brigham Young University).
Wu et al., "Biodegradable hydrophobic-hydrophilic hybrid hydrogels: swelling behavior and controlled drug release", Journal of Biomaterials Science Polymer Edition (J. Biomatter. Sci. Polymer Ed.) (2008) 19 (4): 411-429 (20 pages, including copyright information).
Xin-Zhong Lai et al., "Ceragenins: Cholic Acid-Based Mimics of Antimicrobial peptides", Account of Chemical Research vol. 41, No. 10, Oct. 21, 2008, pp. 1233-1240.
Yin, et al., "Antiangiogenic Treatment Delays Chondrocyte Maturation and Cone Formation During Lim Skeletogenesis", Journal of Bone and Mineral Research, American Society for Bone and Mineral Research, New York, NY, US, vol. 17, No. 1, Jan. 1, 2002.

(56) References Cited

OTHER PUBLICATIONS

Zanger et al., "Structure-Activity Relationship and Drug Design", Remington's Pharmaceutical Sciences, Chapter 27, 16th Edition, 1980, pp. 420-425.

\* cited by examiner

Scheme A-1

Scheme A-2

Scheme B-1

Scheme B-2

METHODS FOR THE SYNTHESIS OF CERAGENINS

CROSS-REFERENCE TO RELATED APPLICATIONS

This application claims the benefit of U.S. Provisional Patent Application No. 62/151,026, filed on Apr. 22, 2015, U.S. Provisional Patent Application No. 62/165,027, filed on May 21, 2015, and U.S. Provisional Patent Application No. 62/191,926, filed on Jul. 13, 2015, the disclosures of which are incorporated herein in their entirety.

BACKGROUND OF THE INVENTION

1. Field

The present application relates to the fields of pharmaceutical chemistry, biochemistry, and medicine. In particular, the present application relates to methods of making cationic steroidal antimicrobials ("CSAs" or "ceragenins").

2. Related Technology

Endogenous antimicrobial peptides, such as the human cathelicidin LL-37, play key roles in innate immunity. LL-37 is found in airway mucus and is believed to be important in controlling bacterial growth in the lung. Antimicrobial peptides are found in organisms ranging from mammals to amphibians to insects to plants. The ubiquity of antimicrobial peptides has been used as evidence that these compounds do not readily engender bacterial resistance. In addition, considering the varied sequences of antimicrobial peptides among diverse organisms, it is apparent that they have evolved independently multiple times. Thus, antimicrobial peptides appear to be one of "Nature's" primary means of controlling bacterial growth. However, clinical use of antimicrobial peptides presents significant issues including the relatively high cost of producing peptide-based therapeutics, the susceptibility of peptides to proteases generated by the host and by bacterial pathogens, and deactivation of antimicrobial peptides by proteins and DNA in lung mucosa.

An attractive means of harnessing the antibacterial activities of antimicrobial peptides without the issues delineated above is to develop non-peptide mimics of antimicrobial peptides that display the same broad-spectrum antibacterial activity utilizing the same mechanism of action. Non-peptide mimics would offer lower-cost synthesis and potentially increased stability to proteolytic degradation. In addition, control of water solubility and charge density may be used to control association with proteins and DNA in lung mucosa.

With over 1,600 examples of antimicrobial peptides known, it is possible to categorize the structural features common to them. While the primary sequences of these peptides vary substantially, morphologies adopted by a vast majority are similar. Those that adopt alpha helix conformations juxtapose hydrophobic side chains on one face of the helix with cationic (positively charged) side chains on the opposite side. As similar morphology is found in antimicrobial peptides that form beta sheet structures: hydrophobic side chains on one face of the sheet and cationic side chains on the other.

We have developed small molecule, non-peptide mimics of antimicrobial peptides, termed ceragenins or CSAs. These compounds reproduce the amphiphilic morphology in antimicrobial peptides, represented above by CSA-13, and display potent, as well as diverse, biological activities (including, but not limited to anti-bacterial, anti-cancer, anti-inflammatory, promoting bone growth, promoting wound healing, etc.). Lead ceragenins can be produced at a large scale, and because they are not peptide based, they are not substrates for proteases. Consequently, the ceragenins represented an attractive compound class for producing pharmaceutically-relevant treatments.

SUMMARY

Certain embodiments described herein relate to methods of making a compound of Formula (I) or Formula (II), comprising the steps of:

(a) reacting a compound of Formula (1) and $R_1R_2$—NH

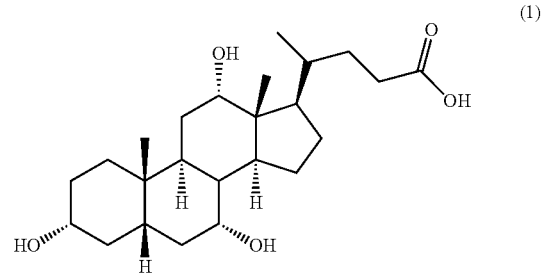

to form a compound of Formula (2):

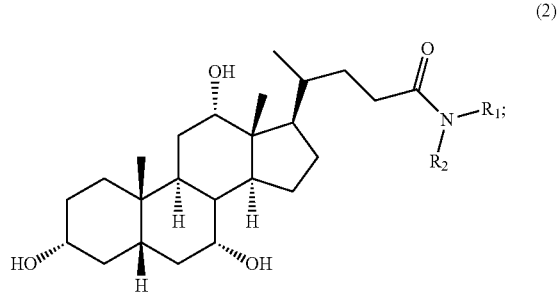

(b) reacting a compound of Formula (2) with a compound of Formula (A),

in the presence of acid and a phase transfer catalyst, to form a compound of Formula (3):

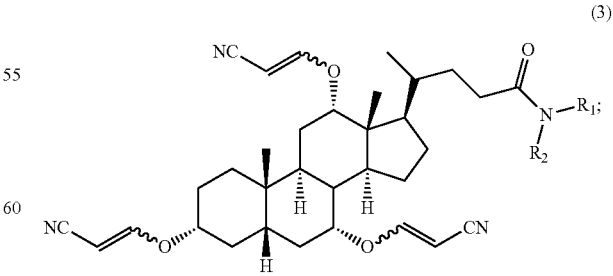

and (c) subjecting a compound of Formula (3) to reducing conditions to form a compound of Formula (I):

(I)

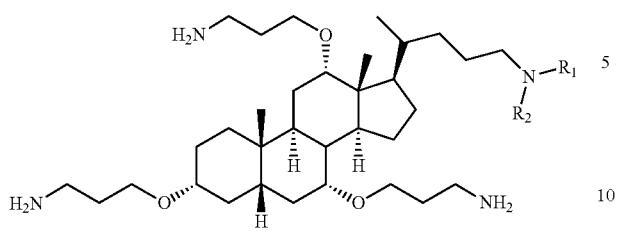

or a compound of Formula (II):

(II)

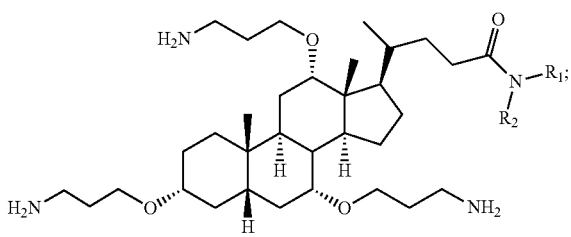

wherein:

$R_1$ and $R_2$ are independently selected from the group consisting of hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, optionally substituted amido, and a suitable amine protecting group; and $R_3$ is selected from the group consisting of optionally substituted $C_1$-$C_{24}$ alkyl, optionally substituted $C_2$-$C_{24}$ alkenyl, optionally substituted $C_2$-$C_{24}$ alkynyl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, and optionally substituted (5 to 10 membered heterocyclyl)-$C_1$-$C_6$ alkyl.

In some embodiments, $R_1$ and $R_2$, together with the atoms to which they are attached form an optionally substituted 5 to 10 membered heterocyclyl ring.

Certain embodiments relate to methods of making a compound of Formula (I) or Formula (II), comprising the steps of:

(a) subjecting a compound of Formula (2) to reducing conditions (2)

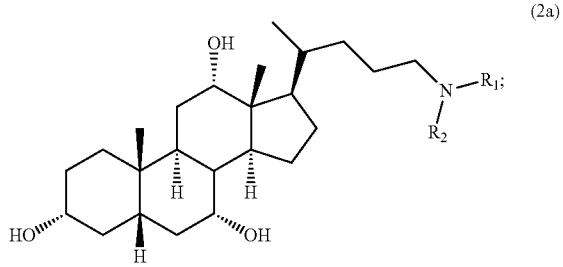

to form a compound of Formula (2a):

(2a)

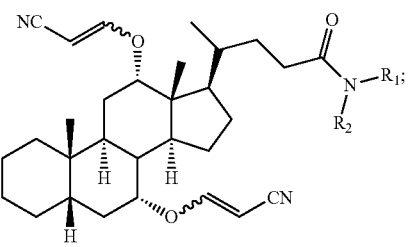

(b) reacting a compound of Formula (2a) with a compound of Formula (A), (A)

in the presence of acid and a phase transfer catalyst, to form a compound of Formula (3):

(3)

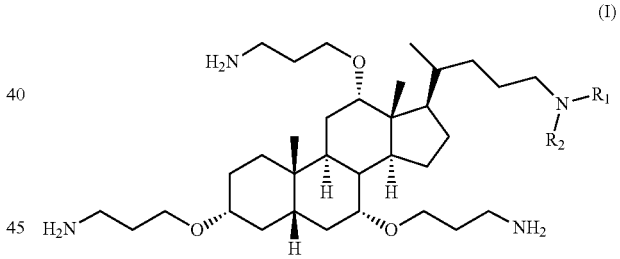

and (c) subjecting a compound of Formula (3) to reducing conditions to form a compound of Formula (I):

(I)

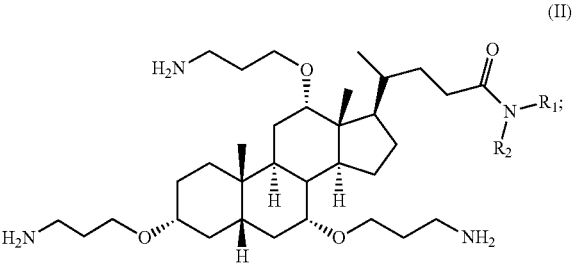

or a compound of Formula (II):

(II)

wherein:

$R_1$ and $R_2$ are independently selected from the group consisting of hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, optionally substituted amido, and a suitable amine protecting group; and $R_3$ is selected from the group consisting of optionally substituted $C_1$-$C_{24}$ alkyl, optionally substituted $C_2$-$C_{24}$ alkenyl, optionally substituted $C_2$-$C_{24}$ alkynyl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, and optionally substituted (5 to 10 membered heterocyclyl)-$C_1$-$C_6$ alkyl.

In some embodiments, $R_1$ and $R_2$, together with the atoms to which they are attached form an optionally substituted 5 to 10 membered heterocyclyl ring.

Advantages of the CSA compounds disclosed herein include, but are not limited to, comparable and/or improved antimicrobial activity, stability, and/or pharmaceutical administerability compared to existing CSA compounds and/or simplified synthesis of final CSA compounds and/or intermediate CSA compounds compared to existing synthetic routes.

Additional features and advantages will be set forth in part in the description that follows, and in part will be obvious from the description, or may be learned by practice of the embodiments disclosed herein. It is to be understood that both the foregoing brief summary and the following detailed description are exemplary and explanatory only and are not restrictive of the embodiments disclosed herein or as claimed.

DETAILED DESCRIPTION

Figure 1:
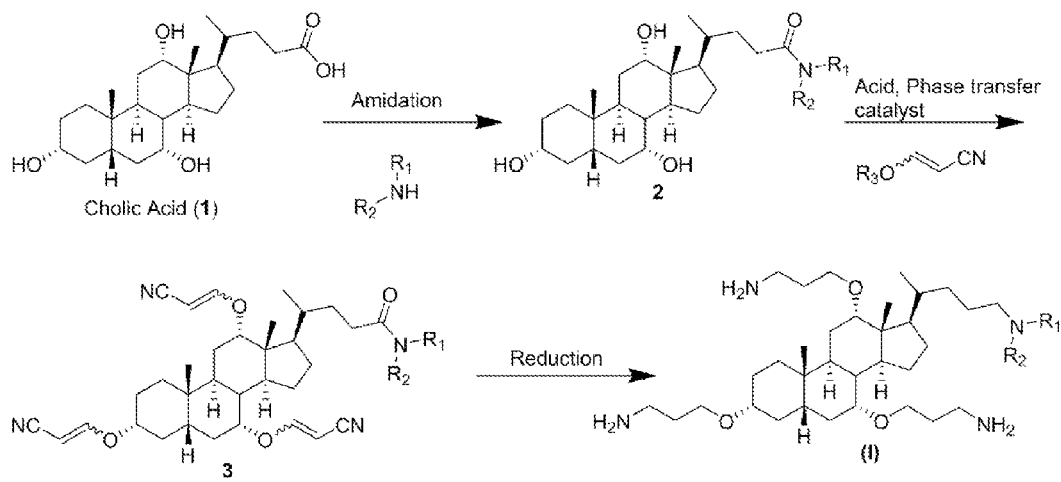
FIG. 1 depicts Scheme A-1, an exemplary but non-limiting general synthetic scheme for preparing a compound of Formula (I).

The embodiments disclosed herein will now be described by reference to some more detailed embodiments, with occasional reference to any applicable accompanying drawings. These embodiments may, however, be embodied in different forms and should not be construed as limited to the embodiments set forth herein. Rather, these embodiments are provided so that this disclosure will be thorough and complete, and will fully convey the scope of the embodiments to those skilled in the art Definitions Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The section headings used herein are for organizational purposes only and are not to be construed as limiting the subject matter described.

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-14}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atom, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

As used herein, "alkylene" means a branched, or straight chain fully saturated di-radical chemical group containing only carbon and hydrogen that is attached to the rest of the molecule via two points of attachment (i.e., an alkanediyl). The alkylene group may have 1 to 20 carbon atoms, although the present definition also covers the occurrence of the term alkylene where no numerical range is designated. The alkylene group may also be a medium size alkylene having 1 to 9 carbon atoms. The alkylene group could also be a lower alkylene having 1 to 4 carbon atoms. The alkylene group may be designated as "$C_{1-4}$ alkylene" or similar designations. By way of example only, "$C_{1-4}$ alkylene" indicates that there are one to four carbon atoms in the alkylene chain, i.e., the alkylene chain is selected from the group consisting of methylene, ethylene, ethan-1,1-diyl, propylene, propan-1,1-diyl, propan-2,2-diyl, 1-methyl-ethylene, butylene, butan-1,1-diyl, butan-2,2-diyl, 2-methyl-propan-1,1-diyl, 1-methyl-propylene, 2-methyl-propylene, 1,1-dimethyl-ethylene, 1,2-dimethyl-ethylene, and 1-ethyl-ethylene.

As used herein, "alkenylene" means a straight or branched chain di-radical chemical group containing only carbon and hydrogen and containing at least one carbon-carbon double bond that is attached to the rest of the molecule via two points of attachment. The alkenylene group may have 2 to 20 carbon atoms, although the present definition also covers the occurrence of the term alkenylene where no numerical range is designated. The alkenylene group may also be a medium size alkenylene having 2 to 9 carbon atoms. The alkenylene group could also be a lower alkenylene having 2 to 4 carbon atoms. The alkenylene group may be designated as "$C_{2-4}$ alkenylene" or similar designations. By way of example only, "$C_{2-4}$ alkenylene" indicates that there are two to four carbon atoms in the alkenylene chain, i.e., the alkenylene chain is selected from the group consisting of ethenylene, ethen-1,1-diyl, propenylene, propen-1,1-diyl, prop-2-en-1,1-diyl, 1-methyl-ethenylene, but-1-enylene, but-2-enylene, but-1,3-dienylene, buten-1,1-diyl, but-1,3-dien-1,1-diyl, but-2-en-1,1-diyl, but-3-en-1,1-diyl, 1-methyl-prop-2-en-1,1-diyl, 2-methyl-prop-2-en-1,1-diyl, 1-ethyl-ethenylene, 1,2-dimethyl-ethenylene, 1-methyl-propenylene, 2-methyl-propenylene, 3-methyl-propenylene, 2-methyl-propen-1,1-diyl, and 2,2-dimethyl-ethen-1,1-diyl.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" refers to RO— and RS—, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro [4.4] nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocylyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

As used herein, "acyl" refers to —C(=O)R, wherein R is hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, as defined herein. Non-limiting examples include formyl, acetyl, propanoyl, benzoyl, and acryl.

An "O-carboxy" group refers to a "—OC(=O)R" group in which R is selected from hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, as defined herein.

A "C-carboxy" group refers to a "—C(=O)OR" group in which R is selected from hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, as defined herein.

A "sulfonyl" group refers to an "—$SO_2$R" group in which R is selected from hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, as defined herein.

An "S-sulfonamido" group refers to a "—$SO_2NR_AR_B$" group in which $R_A$ and $R_B$ are each independently selected from hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, as defined herein.

An "N-sulfonamido" group refers to a "—$N(R_A)SO_2R_B$" group in which $R_A$ and $R_b$ are each independently selected from hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, as defined herein.

An "O-carbamyl" group refers to a "—$OC(=O)NR_AR_B$" group in which $R_A$ and $R_B$ are each independently selected from hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, as defined herein.

An "N-carbamyl" group refers to an "—$N(R_A)OC(=O)R_B$" group in which $R_A$ and $R_B$ are each independently selected from hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, as defined herein.

An "O-thiocarbamyl" group refers to a "—$OC(=S)NR_AR_B$" group in which $R_A$ and $R_B$ are each independently selected from hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, as defined herein.

An "N-thiocarbamyl" group refers to an "—$N(R_A)OC(=S)R_B$" group in which $R_A$ and $R_B$ are each independently selected from hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, as defined herein.

A "C-amido" group refers to a "—$C(=O)NR_AR_B$" group in which $R_A$ and $R_B$ are each independently selected from hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, as defined herein.

An "N-amido" group refers to a "—$N(R_A)C(=O)R_B$" group in which $R_A$ and $R_B$ are each independently selected from hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, or optionally substituted (5 to 10 membered heterocyclyl)-$C_1$-$C_6$ alkyl, as defined herein.

An "amino" group refers to a "—$NR_AR_B$" group in which $R_A$ and $R_B$ are each independently selected from hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, or a suitable amine protecting group, as defined herein. A non-limiting example includes free amino (i.e., —$NH_2$).

An "amide" or "amido" group refers to a "—NR—C(=O)—R group in which each R is independently selected from hydrogen, hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, or a suitable amine protecting group, as defined herein.

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_{24}$ alkyl, $C_1$-$C_{24}$ alkenyl, $C_1$-$C_{24}$ alkynyl, $C_1$-$C_{24}$ heteroalkyl, $C_3$-$C_{10}$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_{10}$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C -amido, N-amido, amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

When two R groups are said to form a ring (e.g., a carbocyclyl, heterocyclyl, aryl, or heteroaryl ring) "together with the atom to which they are attached," it is meant that the collective unit of the atom and the two R groups are the recited ring. The ring is not otherwise limited by the definition of each R group when taken individually. For example, when the following substructure is present:

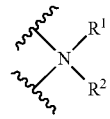

and $R^1$ and $R^2$ are defined as selected from the group consisting of hydrogen and alkyl, or $R^1$ and $R^2$ together with the nitrogen to which they are attached form a heterocyclyl, it is meant that $R^1$ and $R^2$ can be selected from hydrogen or alkyl, or alternatively, the substructure has structure:

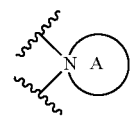

where ring A is a heteroaryl ring containing the depicted nitrogen.

Similarly, when two "adjacent" R groups are said to form a ring "together with the atom to which they are attached," it is meant that the collective unit of the atoms, intervening bonds, and the two R groups are the recited ring. For example, when the following substructure is present:

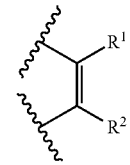

and $R^1$ and $R^2$ are defined as selected from the group consisting of hydrogen and alkyl, or $R^1$ and $R^2$ together with the atoms to which they are attached form an aryl or carbocylyl, it is meant that $R^1$ and $R^2$ can be selected from hydrogen or alkyl, or alternatively, the substructure has structure:

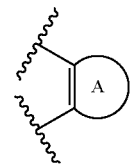

where A is an aryl ring or a carbocylyl containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

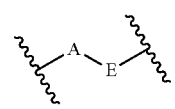

includes the substituent being oriented such that the A is attached at the leftmost attachment point of the molecule as well as the case in which A is attached at the rightmost attachment point of the molecule.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Unless otherwise defined, all technical and scientific terms used herein have the same meaning as commonly understood by one of ordinary skill in the art to which these embodiments belong. The terminology used in the description herein is for describing particular embodiments only and is not intended to be limiting of the embodiments. As used in the specification and the appended claims, the singular forms "a," "an," and "the" are intended to include the plural forms as well, unless the context clearly indicates otherwise. All publications, patent applications, patents, and other references mentioned herein are incorporated by reference in their entirety.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition, it is understood that, in any compound described herein having one or more double bond(s) generating geometrical isomers that can be defined as E or Z, each double bond may independently be E or Z a mixture thereof.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present embodiments. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the embodiments are approximations, the numerical values set forth in the specific examples are reported as precisely as possible. Any numerical value, however, inherently contains certain errors necessarily resulting from the standard deviation found in their respective testing measurements. Every numerical range given throughout this specification and claims will include every narrower numerical range that falls within such broader numerical range, as if such narrower numerical ranges were all expressly written herein. Where a range of values is provided, it is understood that the upper and lower limit, and each intervening value between the upper and lower limit of the range is encompassed within the embodiments.

CSA Compound Synthesis

The methods disclosed herein may be as described below, or by modification of these methods. Ways of modifying the methodology include, among others, temperature, solvent, reagents etc., known to those skilled in the art. In general, during any of the processes for preparation disclosed herein, it may be necessary and/or desirable to protect sensitive or reactive groups on any of the molecules concerned. This may be achieved by means of conventional protecting groups, such as those described in Protective Groups in Organic Chemistry (ed. J. F. W. McOmie, Plenum Press, 1973); and P. G. M. Green, T. W. Wutts, Protecting Groups in Organic Synthesis (3rd ed.) Wiley, N.Y. (1999), which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, Comprehensive Organic Transformations, VCH Publishers, 1989, or L. Paquette, ed., Encyclopedia of Reagents for Organic Synthesis, John Wiley and Sons, 1995, which are both hereby incorporated herein by reference in their entirety. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

An exemplary but non-limiting general synthetic scheme for preparing a compound of Formula (I) is shown in FIG. 1 depicting Scheme A-1. Unless otherwise indicated, the variable definitions are as above for Formula (I). This process starts with a cholic acid (1). Treatment of (1) with secondary amine $R_1R_2NH$ under amide bond forming conditions affords intermediate (2). Amide bond forming reagents include, but are not limited to, EDAC [N-(3-Dimethylaminopropyl)-N'-ethylcarbodiimide hydrochloride] in the presence of HOBT (1-hydroxybenzotriazole), or HATU [N,N,N',N'-Tetramethyl-O-(7-azabenzotriazol-1-yl)uronium hexafluorophosphate) in the presence of diisopropylethylamine, and the like.

In some embodiments, $R_1$ and $R_2$ are independently selected from the group consisting of hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, and a suitable amine protecting group, provided that at least one of $R_1$ or $R_2$ is not a hydrogen.

Compound (2) is treated with an alkoxyacrylonitrile reagent in the presence of acid and a phase transfer catalyst to afford compounds of Formula (3). In some embodiments, the acid is an organic acid. In some embodiments, the acid is an inorganic acid. In some embodiments, the acid is used in catalytic amounts. In some embodiments, the acid is used in stoichiometric amounts. In some embodiments, the acid is used in greater than stoichiometric amounts. In some embodiments, the phase transfer catalyst is tetrabutylammonium iodide. In some embodiments, the phase transfer catalyst is tetrabutylammonium bromide.

Compound (3) is then subjected to reducing conditions to afford compounds of Formula (I). Suitable reducing conditions include, but are not limited to RedAl, lithium aluminum hydride, lithium borohydride, or treatment with hydrogen in the presence of a suitable metal catalyst or treatment with silyl hydrides in the presence of a suitable metal catalyst. Suitable metal catalysts are known in the art.

Figure 2:
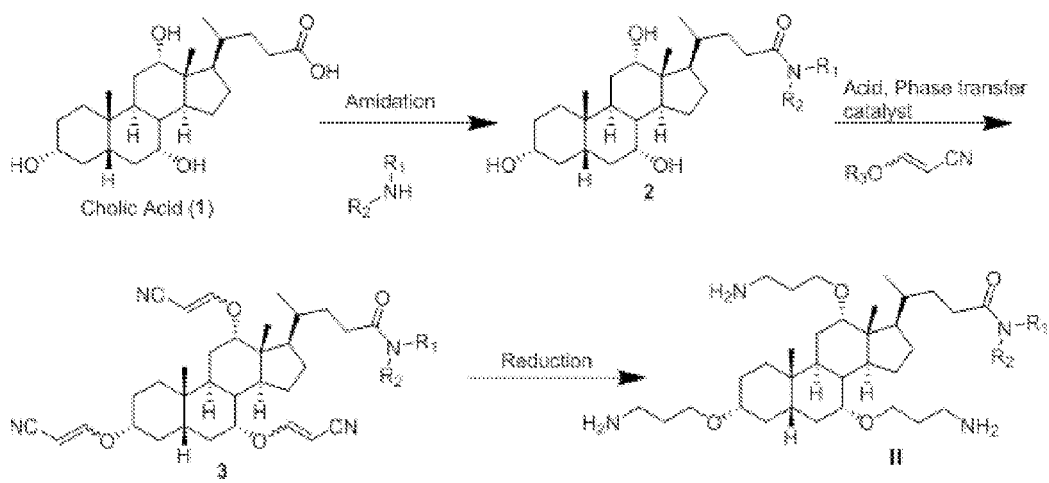
FIG. 2 depicts Scheme A-2, an exemplary but non-limiting general synthetic scheme for preparing a compound of Formula (II).

An exemplary but non-limiting general synthetic scheme for preparing a compound of Formula (II) is shown in FIG. 2 depicting Scheme A-2. Unless otherwise indicated, the variable definitions are as above. This process starts with a cholic acid (1). Treatment of (1) with secondary amine $R_1R_2NH$ under amide bond forming conditions affords intermediate (2). Amide bond forming reagents include, but are not limited to, EDAC [N-(3-Dimethylaminopropyl)-N'-ethylcarbodiimide hydrochloride] in the presence of HOBT (1-hydroxybenzotriazole), or HATU [N,N,N',N'-Tetramethyl-O-(7-azabenzotriazol-1-yl)uronium hexafluorophosphate) in the presence of diisopropylethylamine, and the like.

In some embodiments, $R_1$ and $R_2$ are independently selected from the group consisting of hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, and a suitable amine protecting group, provided that at least one of $R_1$ or $R_2$ is not a hydrogen.

Compound (2) is treated with an alkoxyacrylonitrile reagent in the presence of acid and a phase transfer catalyst to afford compounds of Formula (3). In some embodiments, the acid is an organic acid. In some embodiments, the acid is an inorganic acid. In some embodiments, the acid is used in catalytic amounts. In some embodiments, the acid is used in stoichiometric amounts. In some embodiments, the acid is used in greater than stoichiometric amounts. In some embodiments, the phase transfer catalyst is tetrabutylammonium iodide. In some embodiments, the phase transfer catalyst is tetrabutylammonium bromide.

Compound (3) is then subjected to reducing conditions to afford compounds of Formula (II). Suitable reducing conditions include, but are not limited to RedAl, lithium aluminum hydride, lithium borohydride, or treatment with hydrogen in the presence of a suitable metal catalyst or treatment with silyl hydrides in the presence of a suitable metal catalyst. Suitable metal catalysts are known in the art. The reduction is carried out such that the C-amido group of compound (3) is preferentially not reduced whereas the cyano groups of compound (3) are preferentially reduced.

Figure 3:
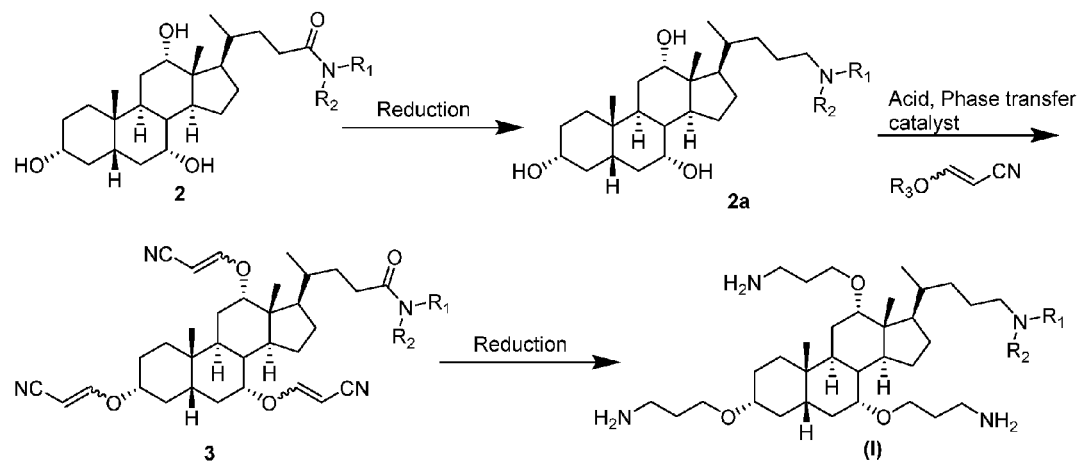
FIG. 3 depicts Scheme B-1, another exemplary but non-limiting general synthetic scheme for preparing a compound of Formula (I).

Another exemplary but non-limiting general synthetic scheme for preparing a compound of Formula (I) is shown in FIG. 3 depicting Scheme B-1. Unless otherwise indicated, the variable definitions are as above for Formula (I).

Compound (2) is subjected to reducing conditions to afford the amine derivative (2a). In some embodiments, suitable reducing agents include, but are not limited to, RedAl, lithium aluminum hydride, lithium borohydride, or treatment with hydrogen in the presence of a suitable metal catalyst or treatment with silyl hydrides in the presence of a suitable metal catalyst. Suitable metal catalysts are known in the art.

Compound (2a) is treated with an alkoxyacrylonitrile reagent in the presence of acid and a phase transfer catalyst to afford compounds of Formula (3). In some embodiments, the acid is an organic acid. In some embodiments, the acid is an inorganic acid. In some embodiments, the acid is used in catalytic amounts. In some embodiments, the acid is used in stoichiometric amounts. In some embodiments, the acid is used in greater than stoichiometric amounts. In some embodiments, the phase transfer catalyst is tetrabutylammonium iodide. In some embodiments, the phase transfer catalyst is tetrabutylammonium bromide.

Compound (3) is then subjected to reducing conditions to afford compounds of Formula (I). Suitable reducing conditions include, but are not limited to RedAl, lithium aluminum hydride, lithium borohydride, or treatment with hydrogen in the presence of a suitable metal catalyst or treatment with silyl hydrides in the presence of a suitable metal catalyst. Suitable systems for the reduction reaction include a catalyst in the presence a of hydrogen atmosphere, in a suitable solvent, with or without the presence of an additive. Suitable catalysts include Raney cobalt, carbon supported palladium, platinum and rhodium catalysts, and sponge metal nickel and cobalt catalysts, and the like. Other metal supported catalysts, such as cobalt on silica, may also be utilized for the hydrogenation reaction, as described in Applied Catalysis A: General 494 (2015) p 41-47, herein incorporated by reference in its entirety. Suitable additives include lithium hydroxide, ammonia, or acidic media. A skilled practitioner will recognize that elevated temperatures and hydrogen pressure may be required. The skilled artisan will also recognize that other reducing agents may be used for the reduction reaction, including the system of nickel chloride and sodium borohydride in an alcohol solvent, such as methanol.

Figure 4:
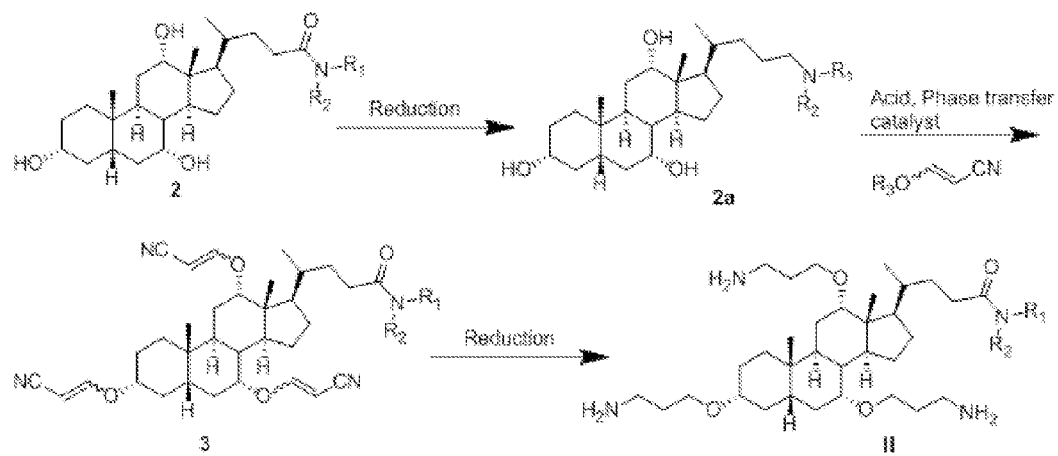
FIG. 4 depicts Scheme B-2, another exemplary but non-limiting general synthetic scheme for preparing a compound of Formula (II).

Another exemplary but non-limiting general synthetic scheme for preparing a compound of Formula (II) is shown in FIG. 4 depicting Scheme B-2. Unless otherwise indicated, the variable definitions are as above.

Compound (2) is subjected to reducing conditions to afford the amine derivative (2a). In some embodiments, suitable reducing agents include, but are not limited to, RedAl, lithium aluminum hydride, lithium borohydride, or treatment with hydrogen in the presence of a suitable metal catalyst or treatment with silyl hydrides in the presence of a suitable metal catalyst. Suitable metal catalysts are known in the art.

Compound (2a) is treated with an alkoxyacrylonitrile reagent in the presence of acid and a phase transfer catalyst to afford compounds of Formula (3). In some embodiments, the acid is an organic acid. In some embodiments, the acid is an inorganic acid. In some embodiments, the acid is used in catalytic amounts. In some embodiments, the acid is used in stoichiometric amounts. In some embodiments, the acid is used in greater than stoichiometric amounts. In some embodiments, the phase transfer catalyst is tetrabutylammonium iodide. In some embodiments, the phase transfer catalyst is tetrabutylammonium bromide.

Compound (3) is then subjected to reducing conditions to afford compounds of Formula (II). The reduction is carried out such that the C-amido group of compound (3) is preferentially not reduced whereas the cyano groups of compound (3) are preferentially reduced. Suitable reducing conditions include, but are not limited to RedAl, lithium aluminum hydride, lithium borohydride, or treatment with hydrogen in the presence of a suitable metal catalyst or treatment with silyl hydrides in the presence of a suitable metal catalyst. Suitable systems for the reduction reaction include a catalyst in the presence a of hydrogen atmosphere, in a suitable solvent, with or without the presence of an additive. Suitable catalysts include Raney cobalt, carbon supported palladium, platinum and rhodium catalysts, and sponge metal nickel and cobalt catalysts, and the like. Other metal supported catalysts, such as cobalt on silica, may also be utilized for the hydrogenation reaction, as described in Applied Catalysis A: General 494 (2015) p 41-47, herein incorporated by reference in its entirety. Suitable additives include lithium hydroxide, ammonia, or acidic media. A skilled practitioner will recognize that elevated temperatures and hydrogen pressure may be required. The skilled artisan will also recognize that other reducing agents may be used for the reduction reaction, including the system of nickel chloride and sodium borohydride in an alcohol solvent, such as methanol.

What is claimed is:

1. A method of making a compound of Formula (I) or (II), comprising the steps of:
    (a) reacting a compound of Formula (1) and $R_1R_2$—NH

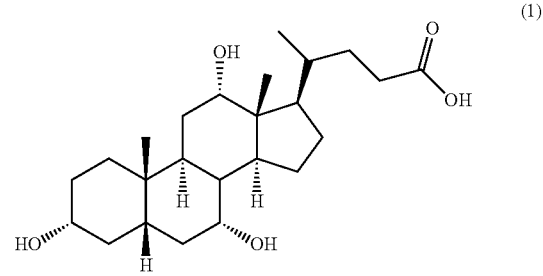

to form a compound of Formula (2):

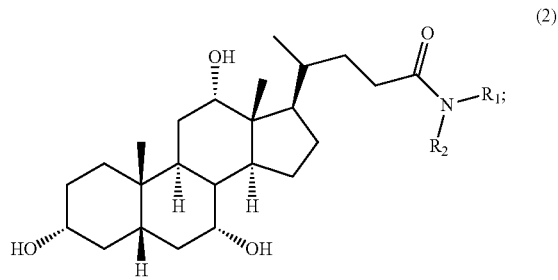

(b) reacting a compound of Formula (2) with an compound of Formula (A),

in the presence of acid and a phase transfer catalyst, to form a compound of Formula (3):

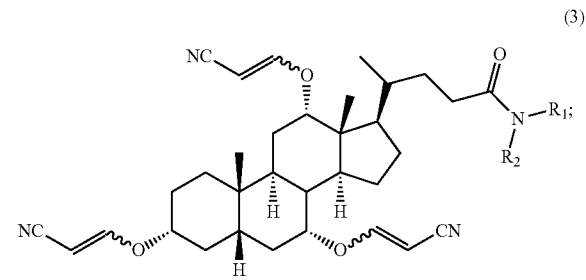

and
(c) subjecting a compound of Formula (3) to reducing conditions to form a compound of Formula (I):

(I)

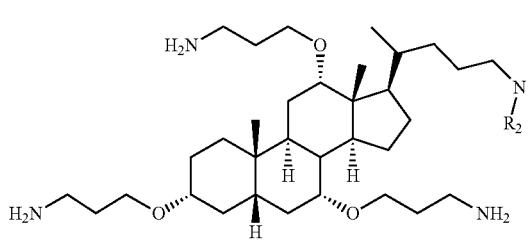

or a compound of Formula (II):

(II)

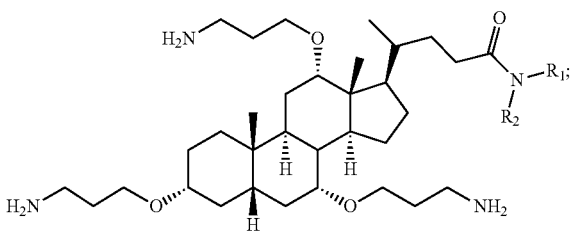

wherein:
R$_1$ and R$_2$ are independently selected from the group consisting of hydrogen, optionally substituted C$_1$-C$_{24}$ alkyl, optionally substituted C$_2$-C$_{24}$ alkenyl, optionally substituted C$_2$-C$_{24}$ alkynyl, optionally substituted C$_6$ or C$_{10}$ aryl, optionally substituted 5 to 10 membered heteroaryl, optionally substituted 5 to 10 membered heterocyclyl, optionally substituted C$_{7-13}$ aralkyl, optionally substituted (5 to 10 membered heteroaryl)-C$_1$-C$_6$ alkyl, optionally substituted C$_{3-10}$ carbocyclyl, optionally substituted C$_{4-10}$ (carbocyclyl)alkyl, optionally substituted (5 to 10 membered heterocyclyl)-C$_1$-C$_6$ alkyl, optionally substituted amido, and a suitable amine protecting group; and
R$_3$ is selected from the group consisting of optionally substituted C$_1$-C$_{24}$ alkyl, optionally substituted C$_2$-C$_{24}$ alkenyl, optionally substituted C$_2$-C$_{24}$ alkynyl, optionally substituted 5 to 10 membered heterocyclyl, optionally substituted C$_{7-13}$ aralkyl, optionally substituted (5 to 10 membered heteroaryl)-C$_1$-C$_6$ alkyl, optionally substituted C$_{3-10}$ carbocyclyl, optionally substituted C$_{4-10}$ (carbocyclyl)alkyl, and optionally substituted (5 to 10 membered heterocyclyl)-C$_1$-C$_6$ alkyl.

2. The method of claim 1, wherein R$_1$ and R$_2$, together with the atoms to which they are attached form an optionally substituted 5 to 10 membered heterocyclyl ring.

3. A method of making a compound of Formula (I) or Formula (II), comprising the steps of:
(a) subjecting a compound of Formula (2) to reducing conditions (2)

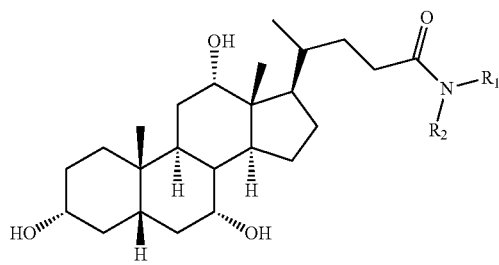

to form a compound of Formula (2a):

(2a)

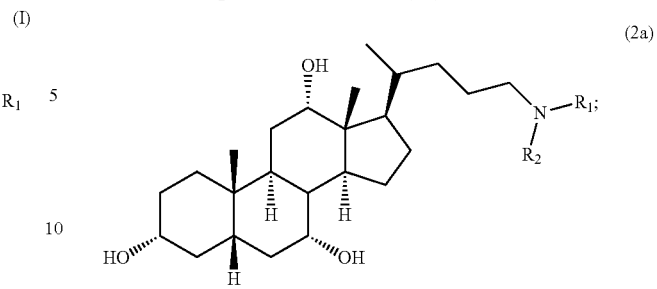

(b) reacting a compound of Formula (2a) with an compound of Formula (A), (A)

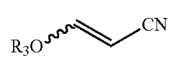

in the presence of acid and a phase transfer catalyst, to form a compound of Formula (3):

(3)

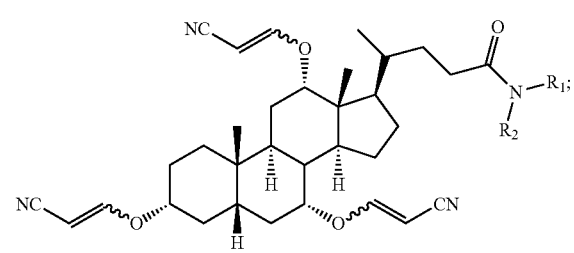

and
(c) subjecting a compound of Formula (3) to reducing conditions to form a compound of Formula (I):

(I)

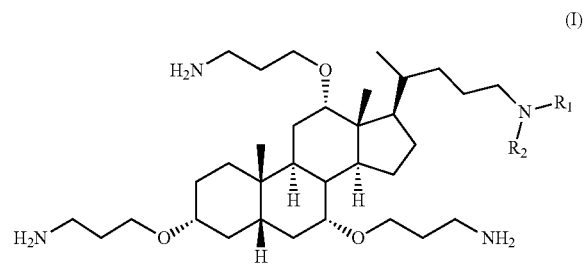

or a compound of Formula (II):

(II)

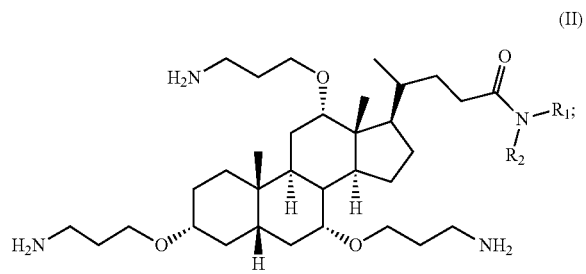

wherein:
R$_1$ and R$_2$ are independently selected from the group consisting of hydrogen, optionally substituted C$_1$-C$_{24}$ alkyl, optionally substituted C$_2$-C$_{24}$ alkenyl, optionally substituted C$^2$-C$_{24}$ alkynyl, optionally substituted C$_6$ or C$_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, optionally substituted amido, and a suitable amine protecting group; and $R_3$ is selected from the group consisting of optionally substituted $C_1$-$C_{24}$ alkyl, optionally substituted $C_2$-$C_{24}$ alkenyl, optionally substituted $C_2$-$C_{24}$ alkynyl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, and optionally substituted (5 to 10 membered heterocyclyl)-$C_1$-$C_6$ alkyl.

4. The method of claim 3, wherein $R_1$ and $R_2$, together with the atoms to which they are attached form an optionally substituted 5 to 10 membered heterocyclyl ring.

5. The method of claim 3, wherein $R_1$ is hydrogen and $R_2$ is selected from the group consisting of hydrogen, optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, optionally substituted (5 to 10 membered heterocyclyl)-$C_1$-$C_6$ alkyl, and a suitable amine protecting group.

6. The method of claim 3, wherein $R_1$ is hydrogen and $R_2$ is selected from the group consisting of optionally substituted $C_1$-$C_{24}$ alkyl, optionally substituted $C_2$-$C_{24}$ alkenyl, optionally substituted $C_2$-$C_{24}$ alkynyl, optionally substituted $C_6$ or $C_{10}$ aryl, optionally substituted 5 to 10 membered heteroaryl, optionally substituted 5 to 10 membered heterocyclyl, optionally substituted $C_{7-13}$ aralkyl, optionally substituted (5 to 10 membered heteroaryl)-$C_1$-$C_6$ alkyl, optionally substituted $C_{3-10}$ carbocyclyl, optionally substituted $C_{4-10}$ (carbocyclyl)alkyl, and optionally substituted (5 to 10 membered heterocyclyl)-$C_1$-$C_6$ alkyl.

7. The method of claim 3, wherein $R_1$ is hydrogen and $R_2$ is optionally substituted $C_1$-$C_{24}$ alkyl.

8. The method of claim 3, wherein the compound of Formula (I) is selected from the group consisting of:

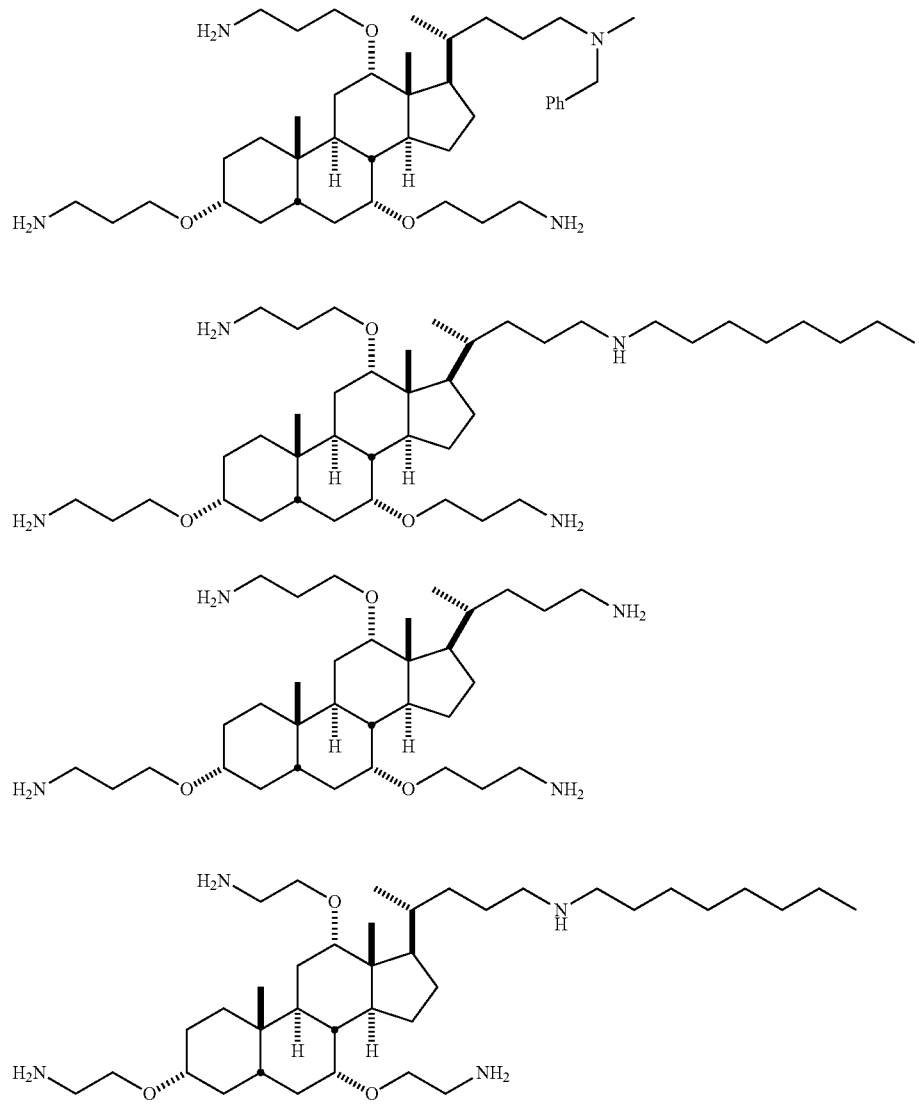

-continued
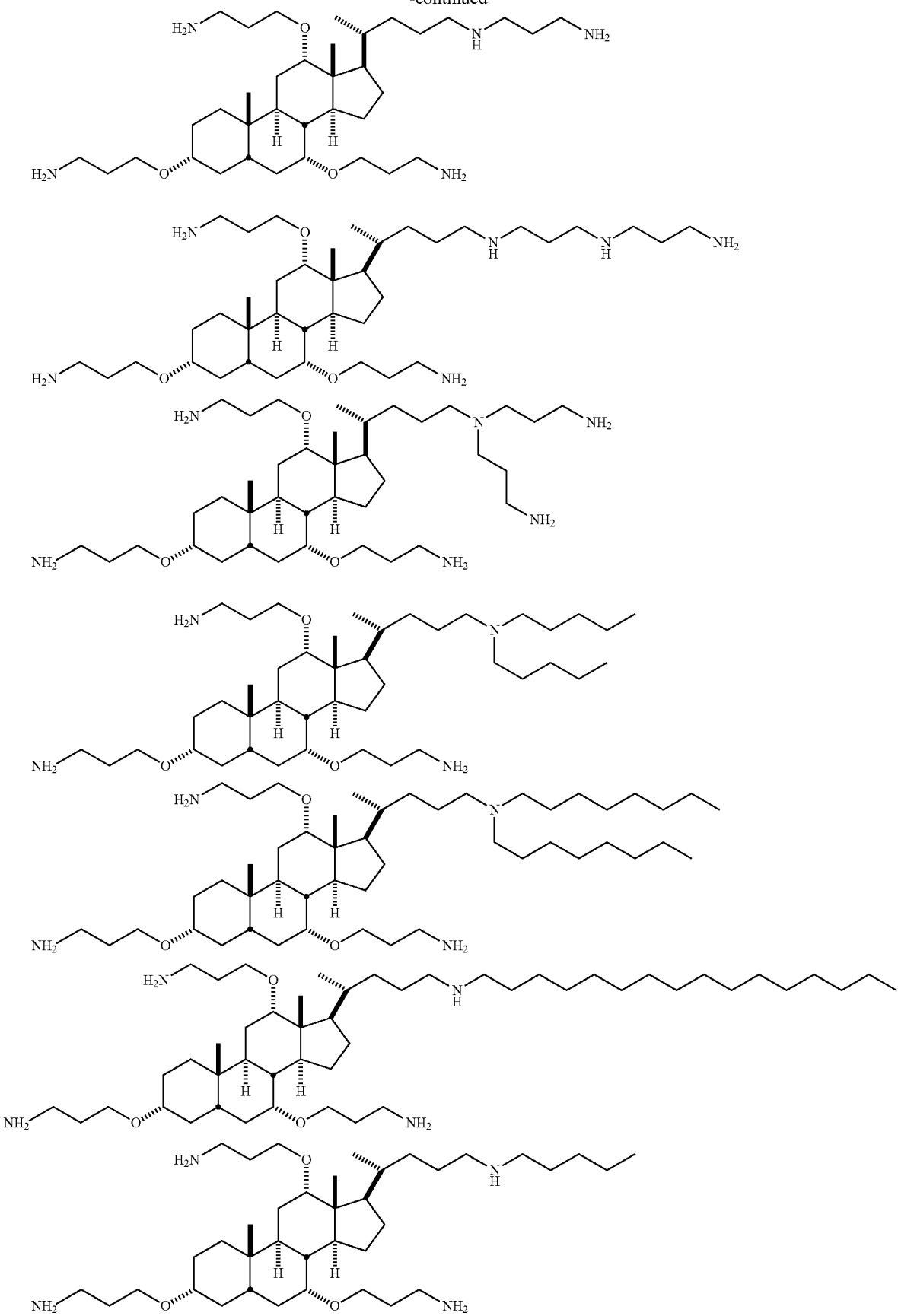

-continued
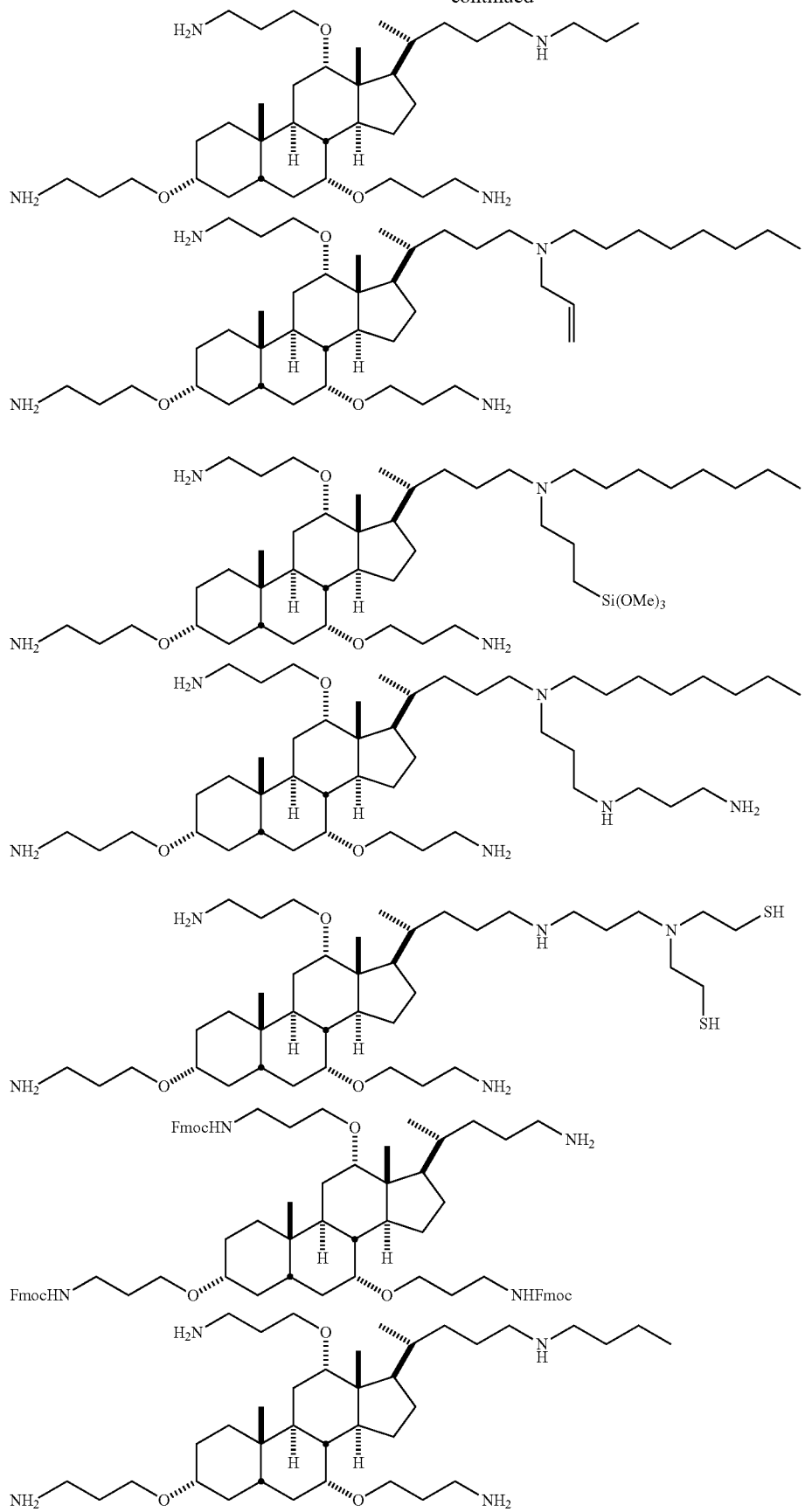

-continued
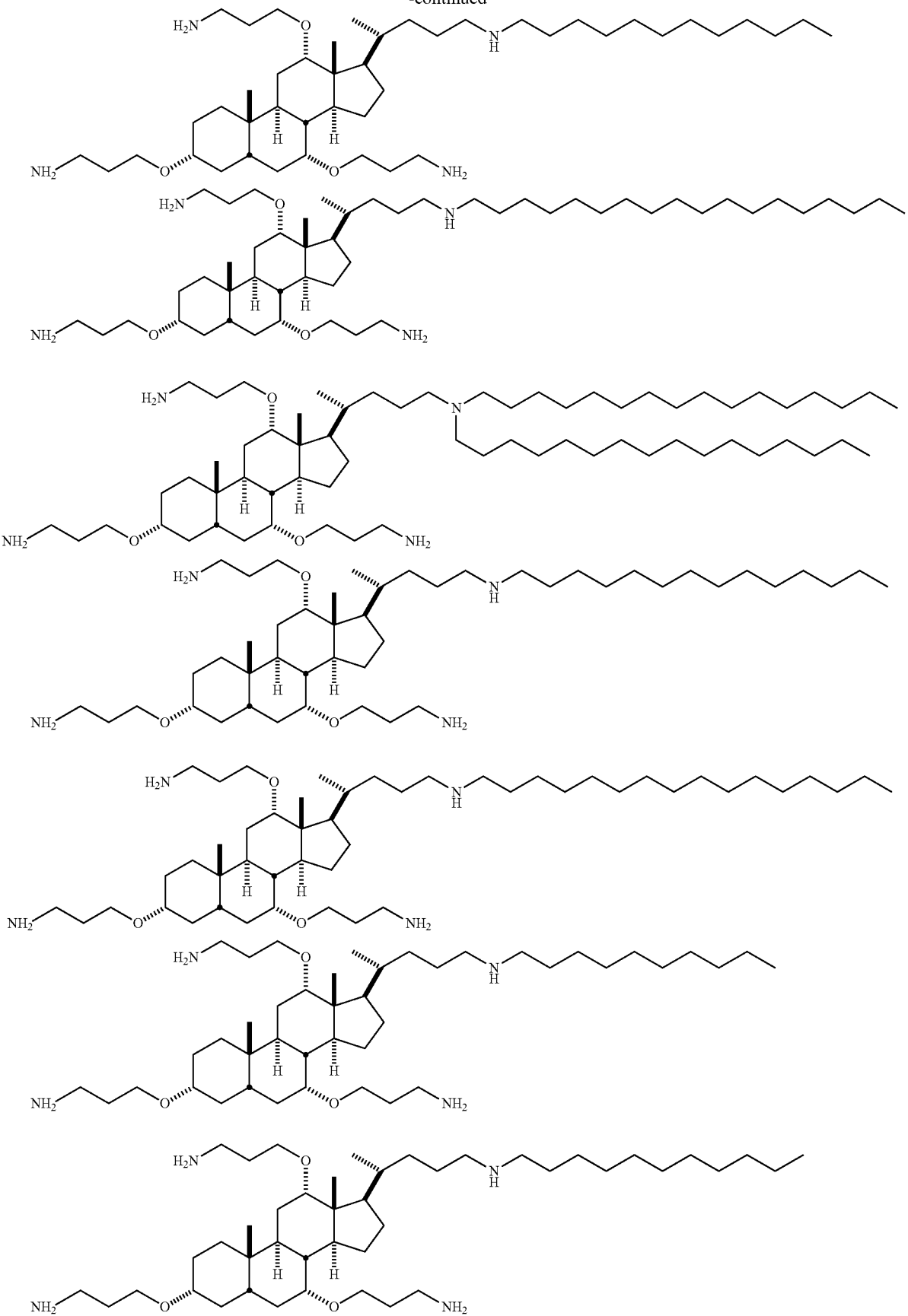

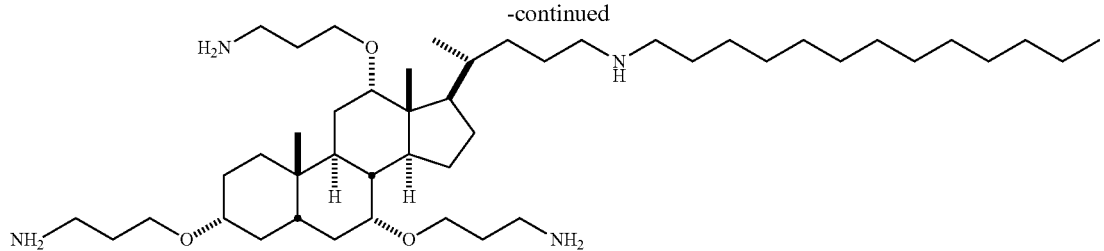
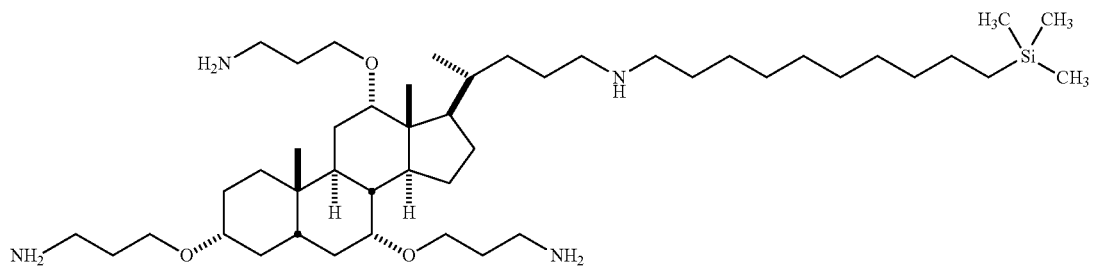
9. The method of claim 3, wherein the compound of Formula (II) is selected from the group consisting of:
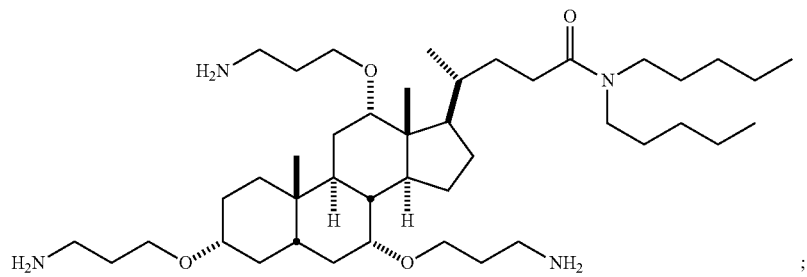
(CSA-190)
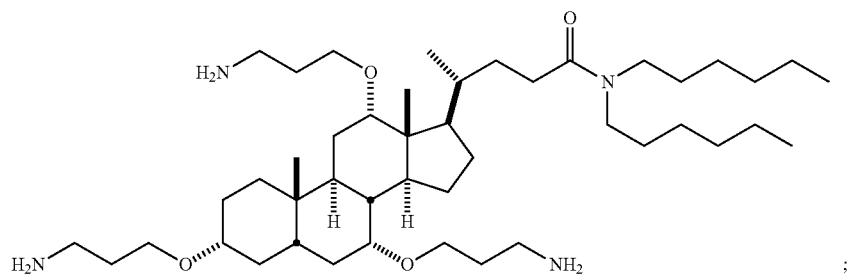
(CSA-191)
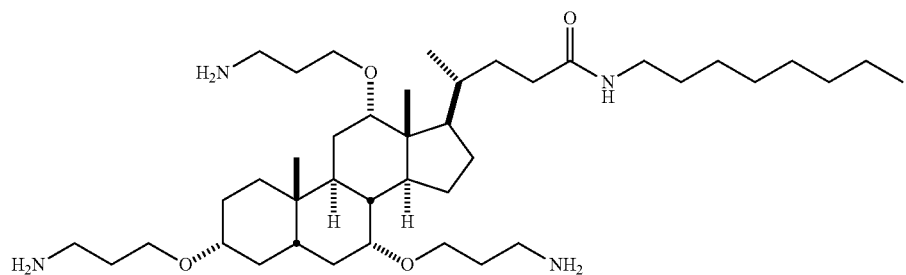
(CSA-192)

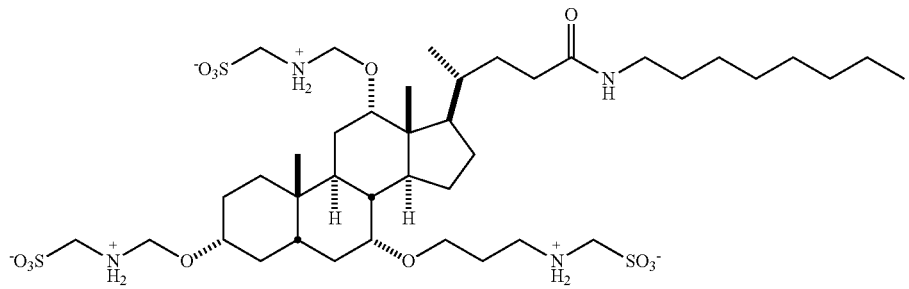

(CSA-192MS)

and salts thereof.

10. The method of claim 3, wherein the method is carried out in one or more solvents selected from the group consisting of water, acetic acid, formic acid, hydrochloric acid, hydrobromic acid, DMF, DMSO, DCM, NMP, chloroform, THF, 2-methyl-THF, benzene, toluene, trifluorotoluene, dioxane, methanol, ethanol, ethyl acetate, acetone, or any combination thereof.

11. The method of claim 3, wherein the method is carried out at a temperature of at least at least 0° C., at least 10° C., at least 20° C., at least 30° C., at least 40° C., at least 50° C., at least 60° C., at least 70° C., at least 80° C., at least 90° C., at least 100° C., at least 110° C., at least 120° C., at least 130° C., at least 140° C., at least 150° C., at least 160° C., at least 170° C., or at least 180° C.

12. The method of claim 3, wherein the method is accomplished in less than 36 hours, less than 35 hours, less than 34 hours, less than 33 hours, less than 32 hours, less than 31 hours, less than 30 hours, less than 29 hours, less than 28 hours, less than 27 hours, less than 26 hours, less than 25 hours, less than 24 hours, less than 23 hours, less than 22 hours, less than 21 hours, less than 20 hours, less than 19 hours, less than 18 hours, less than 17 hours, less than 16 hours, less than 15 hours, less than 14 hours, less than 13 hours, less than 12 hours, less than 11 hours, less than 10 hours, less than 9 hours, less than 8 hours, less than 7 hours, less than 6 hours, less than 5 hours, less than 4 hours, less than 3 hours, less than 2 hours, or less than 1 hour.

13. The method of claim 3, wherein the method provides at least one gram, at least 10 grams, and least 100 grams, at least 500 grams, at least one kilogram, at least 10 kilograms, at least 50 kilograms, at least 100 kilogram, or at least 500 kilograms, of a compound of Formula (I) or a compound of Formula (II).

14. The method of claim 3, wherein the method is substantially performed at ambient pressure.

15. The method of claim 3, wherein the method does not deliberately exclude the presence of oxygen.

16. The method of claim 3, wherein the method is substantially performed in a non-oxygen-containing atmosphere.

17. The method of claim 3, wherein the method is performed with a mixing rate of at least 1 rpm, at least 10 rpms, at least 20 rpms, at least 30 rpms, at least 40 rpms, at least 50 rpms, at least 60 rpms, at least 70 rpms, at least 80 rpms, at least 90 rpms, at least 100 rpms, at least 110 rpms, at least 120 rpms, at least 200 rpms, or at least 500 rpms.

* * * * *

UNITED STATES PATENT AND TRADEMARK OFFICE
CERTIFICATE OF CORRECTION

| | | |
|---|---|---|
| PATENT NO. | : 9,527,883 B2 | Page 1 of 1 |
| APPLICATION NO. | : 15/135900 | |
| DATED | : December 27, 2016 | |
| INVENTOR(S) | : Savage et al. | |

It is certified that error appears in the above-identified patent and that said Letters Patent is hereby corrected as shown below:

In the Specification

Column 1
Line 56, change "As similar" to --A similar--

Column 6
Line 30, change "$C_{1-14}$" to --$C_{1-4}$--

Column 7
Lines 43-44, change "20 carbon atom" to --20 carbon atoms--

Column 16
Line 33, change "E or Z a mixture" to --E or Z or a mixture--
Line 65, change "solvent" to --solvents--

Column 19
Line 13, change "presence a of hydrogen" to --presence of a hydrogen--
Line 59, change "presence a of hydrogen" to --presence of a hydrogen--

In the Claims

Column 22
Line 65, Claim 3 change "$C^2$-$C_{24}$" to --$C_2$-$C_{24}$--

Signed and Sealed this
Eleventh Day of April, 2017

Michelle K. Lee
*Director of the United States Patent and Trademark Office*